United States Patent
Fritz

(10) Patent No.: US 10,940,219 B2
(45) Date of Patent: Mar. 9, 2021

(54) RADIOACTIVE MICROSPHERES MADE OF NANOPOROUS GLASS FOR RADIATION THERAPY

(71) Applicant: SphereRx, LLC, Seattle, WA (US)

(72) Inventor: Eberhard Fritz, Berlin (DE)

(73) Assignee: SphereRx, LLC, Seattle, WA (US)

( * ) Notice: Subject to any disclaimer, the term of this patent is extended or adjusted under 35 U.S.C. 154(b) by 0 days.

(21) Appl. No.: 16/506,174

(22) Filed: Jul. 9, 2019

(65) Prior Publication Data

US 2019/0336624 A1 Nov. 7, 2019

Related U.S. Application Data

(63) Continuation of application No. 15/033,298, filed as application No. PCT/DE2014/000561 on Oct. 30, 2014, now abandoned.

(30) Foreign Application Priority Data

Nov. 1, 2013 (DE) .................... 10 2013 018 685.4

(51) Int. Cl.
*A61K 51/12* (2006.01)
*A61K 51/02* (2006.01)

(52) U.S. Cl.
CPC .......... *A61K 51/1255* (2013.01); *A61K 51/02* (2013.01)

(58) Field of Classification Search
CPC ............................ A61K 51/1255; A61K 51/02
See application file for complete search history.

(56) References Cited

U.S. PATENT DOCUMENTS

2016/0151518 A1* 6/2016 Stephens ............ A61K 51/1244
424/1.37

* cited by examiner

*Primary Examiner* — Robert S Cabral
(74) *Attorney, Agent, or Firm* — Etherton Law Group, LLC

(57) ABSTRACT

Microspheres made of solid glass are used in radiation therapy, wherein the radiotherapeutic radionuclide must be generated in the glass by neutron activation. Microspheres of this type have a high radioactive load, are relatively heavy and contain additional non-therapeutic radionuclides. Additionally, radioactive microspheres made of plastic are used, which can be loaded with radionuclides by chemical means. These microspheres have a lower loading capacity, no additional radionuclides, and are lighter. The therapeutic radionuclide in both cases is Y-90. Microspheres made of nanoporous glass contain the therapeutic radionuclide, have a high loading capacity, require no neutron activation, can be parallel charged with multiple therapeutic and with diagnostic radionuclides, and are very light. It is possible to produce them in a radiochemical laboratory. Microspheres of this type can also be used diagnostically in preparation for therapy. For this purpose, they can be provided in a therapeutically or diagnostically specified quantity and radioactivity.

6 Claims, No Drawings

RADIOACTIVE MICROSPHERES MADE OF NANOPOROUS GLASS FOR RADIATION THERAPY

BACKGROUND

Radioactive microspheres for tumor therapy have a spherical geometry and contain a therapeutic radionuclide, usually yttrium-90 (Y-90). They are used in the treatment of non-operable liver tumors. The method is known as Selective Internal Radiation Therapy (SIRT) or radioembolization. More than a million patients fall ill from liver tumors across the world each year, with predominantly poor prognosis. Radiation therapy with radioactive microspheres improves the quality of life of affected patients and extends survival.

To date, two types of microspheres have been used. They differ in their physical parameters and their manufacturing process. Salem 2006 gives an overview of the use of microspheres by the NORDION (Canada), now BTG, and SIRTEX Medical (Australia) companies. In an earlier review, Häfeli 2001 summarised the therapeutic value of the microspheres. In both variants, Radionuclide Y-90 beta radiation is used therapeutically.

NORDION (TheraSphere®) generates the Y-90 by neutron activation in a nuclear reactor from non-radioactive Y-89, added in the glass manufacturing process. NORDION uses the technology disclosed in the patents U.S. Pat. Nos. 4,789,501 and 5,011,677 (University of Missouri, USA). Neutron activation however not only generates the Y-90 radionuclide in the glass microspheres but also other unwanted radionuclides that are sometimes harmful in treatment. This effect can be mitigated but not completely avoided by extending the interval between neutron activation and therapy. The current state of knowledge on therapy using TheraSphere® is summarised in a bibliography (NORDION 2013).

The Sirtex company's microspheres use the ability of resin spheres to bind a certain amount of Y-90 to the surface ionically. Sirtex has disclosed the technology for production and use of radioactive resin spheres (WO 02/34300 AI; US 2007/0253898 A1, US 2010/0215571 AI). Sirtex 2013 contains a bibliography of publications on the use of Sir-Spheres®.

SIRTEX has also made a patent disclosure on the production of radioactive glass microspheres (U.S. Pat. No. 6,998,105) describing how the weight of the solid spheres can be reduced by modifying the molten glass mix, thus eliminating the disadvantage of high glass density. An achievable density of less than 2.5 g/cm$^3$ is specified, as compared to a density of greater than 3 g/cm$^3$ in NORDION microspheres. The minimum density achievable by SIRTEX is less than 2.2 g/cm$^3$, with an absolute minimum of 2.13 g/cm$^3$. The radionuclide Y-90 to be loaded, achieved as in the NORDION process by neutron activation of Y-89, is fixed to the surface of non-porous glass. However, the invention does not in principle reduce the formation of unwanted radionuclides in neutron activation.

There are no known radioactive microspheres by other manufacturers, apart from the NORDION full glass microspheres (TheraSphere®) and Sirtex resin microspheres (SIR-Spheres®).

EP 0210875 (Theragenics Corporation, USA) disclosed a system for delivering the microspheres to a vascular tumor. This system is currently used worldwide by the NORDION company. Another system is disclosed in U.S. Pat. No. 4,745,907 (Nuclear Medicine Inc., USA) for delivering small radioactive particles, such as microspheres, to liver tumors.

SUMMARY

One object of the invention is to produce radioactive microspheres for the treatment and diagnosis of tumors with vascular supply, especially liver tumors. The radionuclide is bound to the microsphere in such a way that it is not leached or released into the tumor, instead only emitting the ionizing radiation for the treatment of the tumorous tissue.

A further object is to produce glass microspheres without radiochemical impurities, with a similar or lower weight to resin microspheres of the same size.

A further object is the loading of the microspheres with radionuclides by conventional physical and chemical methods and devices in radionuclide laboratories without the use of nuclear reactors for neutron activation. One option of this object allows the simple loading technology to be kept very simple indeed, facilitating use in specialized radiopharmaceutical or chemical laboratories of hospitals, thus enabling these institutions to provide rapid patient care.

A further object is an option involving loading of microspheres for diagnostics in nuclear medicine using radionuclides, which act primarily as photon emitters and ensure accurate diagnostic preparation of therapy and follow-up controls.

A further object of the invention is multiple loading of microspheres with therapeutic and diagnostic radionuclides.

The invention is a radiation therapy product of spherical nanoporous glass beads that are loaded with a radionuclide. Each microsphere has a diameter in the range of about 25 to 60 microns. The pore structure of each microsphere can occupy between about 30 and 90 percent of the microsphere's volume, and the inner surface area measures between about 30 and 500 m$^2$/g. One or more radionuclides is embedded in the nanopores of each microsphere. In a preferred embodiment the product has at least two radionuclides, a first radionuclide achieves a therapeutic effect and a second radionuclide has nuclear medical diagnostic properties. Preferably the therapeutic radionuclide is Y-90 and the diagnostic radionuclide is In-111, Ga-68, or Ga-67. In a preferred embodiment the radionuclides are made less soluble or insoluble in blood components to avoid washing the radionuclide away.

DETAILED DESCRIPTION OF THE INVENTION

The objects of the invention are achieved by the use of microscopically small nanoporous glass beads with a spherical geometry, which are loaded with a radionuclide of the highest radiochemical purity.

The microspheres have a physical size within the range of 25 to 60 µm. The microsphere pores have a size within the range of 5 to 400 nm. The pore structure can occupy between 30 and 90 percent of a microsphere's volume. The inner surface of the nanoporous glass thus provided for loading is much greater than the outer surface, measuring between 30 and 500 m$^2$/g.

The effective (apparent) density of the nanoporous glass depends on the void content of the glass. In aqueous solutions, a high void content means that the effective density of the microspheres will be closer to but slightly greater than the density of the aqueous solution. This property of the nanoporous glass allows an effective microsphere density of less than 2.2 g/cm³ to be achieved, which corresponds to the minimum density of pure nonporous silica. Ideally, an effective microsphere density of less than 1.5 g/cm³ is achieved during radiotherapy.

The nanoporous microspheres take the radionuclide up during loading and retain it in the pores during therapy following a fixing procedure. The loading and fixing of one or more radionuclides can be achieved using normal laboratory chemical and physical procedures and devices available in the prior art. No neutron activation is used for the manufacture of microspheres given the commercial availability of high purity radionuclides for loading, such as Y-90 and In-111.

Y-90 is preferred for use as a therapeutic radionuclide. Diagnostic radionuclides are chosen from the group Indium 111 (In-111), Gallium-68 (Ga-68). High-purity Y-90 and In-111 can be purchased commercially, for instance from by the Perkin-Elmer company (Canada). Ga-68 is obtained from radionuclide generators.

Both nanoporous glass and the way it is produced are well-known and form part of the prior art. The product and its manufacture is described for example in DD 250 471 AI; DD 143 898 AI; DE 196 33 257 C1 and DE 410 26 35 AI (VitraBio GmbH, Steinach, Germany). The loading of the radionuclide contained in a chemical solution onto the microspheres is achieved by means of incubation in the exposed surface pore system. The pore system inside the spheres is a surface-connected channel system in which each pore has an opening hole to the surface. All pores can be loaded from the surface through these holes.

Subsequently, the solution is dried into the pore system and the chemical compound is calcined. Thermal treatments of the incubated microspheres should preferably be used, with the required decomposition temperature for the chemical compound of the radionuclide. Other alternative methods like the use of microwaves or light, for example, may be used with suitable chemical compounds. In the process, the radionuclide is preferably converted into its oxide inside the void volume, which is then deposited in the void volume of the inner surfaces. Gaseous decomposition products escape and non-gaseous products can be washed away with suitable solvents. Some radionuclide oxides are dissolvable by blood components, causing unwanted leaching or washing away of the radionuclide. Such oxides, for example yttrium oxide, may be converted in a further step to another compound that is far less soluble or insoluble in the blood. Conversion may be achieved, for example, by addition of acids such as hydrofluoric acid, oxalic acid, sulphuric acid, sulphurous acid or phosphoric acid at very low concentrations. In a further step, the isolated radionuclide, the oxide or the optionally obtained low solubility compounds of the radionuclide may be thermally baked onto the glass, thus lowering its propensity to being leached or washed away. This is done at temperatures below the decomposition temperature of the compounds. In one embodiment, yttrium oxide (yttria) can chemically bind with the glass surface once embedded in the pore structure during high temperature treatment of the microspheres.

Additional optional steps may also be taken for the surface finishing of the microspheres. For example, the suspensibility and mechanical flow of the microspheres in vascular application can be improved by hydrophobization.

Another option is the simultaneous loading of two different radionuclides, wherein a first radionuclide achieves a therapeutic effect and a second radionuclide has nuclear medical diagnostic properties. For this purpose radionuclides are used with similar chemical and physical properties to those in the manufacturing steps, such as Y-90 and In-111 or Ga-67 and Ga-68.

Compounds of the radionuclide that can only be dissolved in organic solvents are also suitable for the loading process. Fixing is carried out by evaporation of the solvent and baking of the compound into the nanoporous structure. Another embodiment of the loading process is loading by the clinical users themselves (e.g. in the clinical radiopharmaceutical centre). The latter receive the raw materials and implement the prescribed loading steps in their own laboratory (kit solution).

SIRT tumor treatment involves injection of a very high number of loaded microspheres into the vascular supply of the tumor. The microspheres are blocked in the arteries of the tumor due to their large diameter. The tumor is then treated by radioembolization. Radioactive loading of the total number of microspheres for the tumor site is set sufficiently high to deliver a radiation dose of between 80 and 150 Gray to the tumor. Given the very high load variability of nanoporous microspheres, the number of microspheres in a single tumor dose can be set within a range of less than 1 million to several millions, something that could not be achieved to date with existing microspheres. This allows new therapeutic approaches. The number of microspheres per tumor in the case of tumors with a diameter of a few centimetres can be set at between one and four million.

Simple loading and fixing procedures mean that the above-mentioned kit solution can be used for production in the clinical environment.

The possibility of double loading of therapeutic and diagnostic radionuclides meets the need in radiation medicine for follow-up controls during and after the therapy, again something that could not be achieved with existing microspheres.

Embodiment 1

The therapeutic treatment plan based on the radiologically assessed size of the liver tumor provides for catheter application of 20 GBq of Y-90 activity and four million microspheres.

The 20 GBq of activity selected for loading is intended to compensate for radioactive decay during manufacture and logistical delivery. Y-90 is used as a nitrate in a nitric acid solution. The porosity of the microspheres is 75%. The effective density in aqueous solutions is therefore 1.4 g/mm³. The average diameter of the microspheres is 30 µm.

Production is patient-specific based on the requirements of the oncologists, in other words the patient dose in this example is prepared for one given particular patient only.

The following steps are to be implemented in order:

Weigh out 38 mg (approximately 76 µl) of microspheres, equivalent to the required number of 4 million.

Triple-wash the microspheres in distilled water and then dry them at 105° C.

Prepare the radioactive loading solution of 20 GBq Y-90-nitrate in 60 µl 0.05 M $HNO_3$ (approximately equivalent to the void volume of the microspheres).

Place the microspheres in an Eppendorf tube and drip on the 60 µl of Y-90 loading solution.

Place the unsealed Eppendorf tube in a desiccator and evacuate to 10 mbar for about one hour.

Dry the unsealed Eppendorf tube in a drying cabinet, slowly raising the temperature from 60 to 105° C.

Transfer the microspheres to a porcelain combustion boat and slowly heat in a furnace to 600° C. and maintain temperature for one hour.

After they have cooled, transfer the microspheres to a new Eppendorf tube and triple wash in 1 ml of distilled water, centrifuge, then dry in heating cabinet at 80° C. for one hour.

Drip on 60 µl of 0.005 M HF and incubate in a desiccator at 10 mbar for 10 minutes, followed by 30 minutes reaction time in a heating cabinet at 30° C. in the Eppendorf tube.

Dry in the heating cabinet at 105° C. for the complete removal of the non-converted HF.

Transfer the microspheres to porcelain combustion boats and bake in the yttrium fluoride at 750° C.

Transfer the microspheres to an Eppendorf tube.

Triple wash with 1 ml distilled water, with subsequent removal of water by centrifuging.

Measure the load activity in an ionization chamber.

Transfer the microspheres by absorption with 1.5 ml physiological saline solution to a sterilisable V-Vial (3 ml) and seal with a sterilisable crimp seal Autoclave.

After autoclaving, the microspheres can be used after about six days, after they have reached the required activities by radioactive decay. Prior to application to the patient's tumor, a further metrological activity control should be performed by a medical physicist.

Embodiment 2

Shunt determination is necessary during preparation for tumor treatment to clarify whether the patient is suitable for liver tumor treatment using microspheres. The shunt measures the loss of microspheres that would not be retained in the liver tumor but would rather be deposited as unwanted in other parts of the body.

Diagnostic imaging using nuclear medicine techniques can be performed with the In-111 radionuclide. A load activity of 200 MBq is selected and the number of microspheres is weighed at 400,000.

Subsequent steps are to be performed as described in Embodiment 1. The amount of microspheres used is correspondingly reduced to 3.8 mg and the amounts of $HNO_3$ and HF adjusted to 6 µl. Indium fluoride is formed and baked in as the insoluble compound.

What is claimed is:

1. A process for making radioactive glass microspheres for radiation therapy, wherein each glass microsphere has nanopores and each nanopore has a surface, the process comprising:
   a. loading the nanopores of the nanoporous glass microspheres with a loading solution comprising a radionuclide in a first acid;
   b. evaporating the loading solution until the radionuclide precipitates onto the surface of the nanopores in the microspheres;
   c. thermally treating the microspheres so that precipitated radionuclide salt is converted into a low-solubility or insoluble form and is affixed to the surface of the nanopores; and
   d. applying a second acid to the microspheres after thermally treating them, where the second acid is one or more of hydrofluoric acid, oxalic acid, sulphuric acid, sulphurous acid, or phosphoric acid.

2. The process of claim 1 further comprising evaporating the second acid from the microspheres.

3. The process of claim 2 wherein the evaporation of the second acid is accomplished by vacuum.

4. A process for making radioactive glass microspheres for radiation therapy, wherein each glass microsphere has nanopores and each nanopore has a surface, the process comprising:
   a. loading the nanopores of the nanoporous glass microspheres with a loading solution comprising a radionuclide in a first acid wherein the radionuclide is a nitrate and the first acid is nitric acid;
   b. evaporating the loading solution until the radionuclide precipitates onto the surface of the nanopores in the microspheres; and
   c. thermally treating the microspheres so that precipitated radionuclide salt is converted into a low-solubility or insoluble form and is affixed to the surface of the nanopores.

5. A process for making radioactive glass microspheres for radiation therapy, wherein each glass microsphere has nanopores and each nanopore has a surface, the process comprising:
   a. loading the nanopores of the nanoporous glass microspheres with a loading solution comprising a radionuclide in a first acid wherein the radionuclide is selected from Y-90 and In-111;
   b. evaporating the loading solution until the radionuclide precipitates onto the surface of the nanopores in the microspheres;
   c. thermally treating the microspheres so that precipitated radionuclide salt is converted into a low-solubility or insoluble form and is affixed to the surface of the nanopores.

6. A process for making radioactive glass microspheres for radiation therapy, wherein each glass microsphere has nanopores and each nanopore has a surface, the process comprising:
   a. saturating the nanopores of the nanoporous glass microspheres with a loading solution comprising a radionuclide in an acid, until the nanopores are filled with the loading solution wherein the radionuclide is selected from Y-90 and In-111; and
   b. thermally treating the microspheres until the radionuclide precipitates onto the surface of the nanopores in the microspheres and the precipitated radionuclide salt is converted into a low-solubility or insoluble form and is affixed to the surface of the nanopores.

* * * * *